United States Patent [19]
Raines et al.

[11] Patent Number: 5,840,296
[45] Date of Patent: Nov. 24, 1998

[54] ENGINEERED CYTOTOXIC RIBONUCLEASE A

[76] Inventors: Ronald T. Raines, 2320 Lakeland Ave., Madison, Wis. 53704; Peter A. Leland, 4849 Sheboygan Ave. #321, Madison, Wis. 53705; L. Lane Schultz, 2152 Allen Blvd., Apartment No. 1, Middleton, Wis. 53562

[21] Appl. No.: 950,866

[22] Filed: Oct. 15, 1997

[51] Int. Cl.⁶ .............................. A61K 38/46; C12N 9/16; C12N 9/22
[52] U.S. Cl. ......................... 424/94.6; 435/196; 435/199; 935/10
[58] Field of Search ..................................... 435/199, 196; 424/94.6; 935/10

[56] References Cited

U.S. PATENT DOCUMENTS 5,389,537  2/1995  Raines et al. ........................... 435/199

OTHER PUBLICATIONS

Alfacell Corporation, Reports and Press Releases from Oct. 1994–Nov. 1996.
Delmonte, "Novel Ribonuclease Shows Antitumor Activity in Pancreatic Cancer and Mesothelioma", Onclology Times 18 No. 6, 1996.
Kim et al., "Mechanism of Ribonuclease Cytotoxicity", J. Biol. Chem. 270 No. 52: 31097–31102, 1995.
Kim et al., "Structural Basis for the Biological Activities of Bovine Seminal Ribonuclease", J. Biol. Chem. 270, No. 18: 10525–10530, 1995.
Kobe and Deisenhofer, "A Structural Basis of the Interactions Between Leucine–Rich Repeats and Protein Ligands", Nature 374, No. 9: 183–186, 1995.
Raines et al., "Replacing a Surface Loop Endows Ribonuclease A with Angiogenic Activity", J. Biol. Chem. 270, No. 29: 17180–17184, 1995.
Schein, "From Housekeeper to Microsurgeon: The Diagnostic and Therapeutic Potential of Ribonucleases", Nature Biotechnology 15: 529–536, 1997.

*Primary Examiner*—Keith D. Hendricks
*Attorney, Agent, or Firm*—Quarles & Brady

[57] ABSTRACT

Modified ribonucleases belonging to the RNase A superfamily of ribonucleases is disclosed. Each modified ribonuclease has a mutation in the loop region corresponding to amino acids 85–94 of bovine pancreatic RNase A. Each modified ribonuclease has reduced binding affinity for ribonuclease inhibitor (RI), wild-type ribonuclease activity, and exhibits enhanced cytotoxicity toward tumor cells, relative to the wild-type ribonuclease. Also disclosed is a method for obtaining a modified ribonuclease having reduced binding affinity for RI, wild-type ribonuclease activity, and enhanced cytotoxicity.

9 Claims, 1 Drawing Sheet

ENGINEERED CYTOTOXIC RIBONUCLEASE A

STATEMENT REGARDING FEDERALLY SPONSORED RESEARCH OR DEVELOPMENT

This invention was made with government support through grant CA73808 awarded by the National Institutes of Health. The United States Government has certain rights in this invention.

BACKGROUND OF THE INVENTION

The development of new drugs has contributed to the progress that has been made in recent years in the treatment of various types of cancer. However, certain cancers are refractory to the chemotherapeutic agents that are currently in use. These malignancies tend to be particularly virulent and are associated with a high mortality rate. Most existing chemotherapeutic agents have undesirable side effects as well. Consequently, there is ongoing interest, both within the medical community and among the general population, in the development of novel chemotherapeutic agents for the treatment of malignant tumors and other types of cancer.

One naturally occurring ribonuclease isolated from the leopard frog (Rana pipiens) has shown antitumor activity in patients with advanced inoperable pancreatic cancer and malignant mesothelioma in PhaseI/II studies (Delmonte, Oncology Times Vol. 18, No. 8, August 1996). The antitumor activity of this ribonuclease (referred to as Onconase) has been examined in more than 350 patients with a variety of solid tumors and has been shown to have antitumor activity against metastatic pancreatic carcinoma, advanced metastatic breast cancer, and malignant mesothelioma. Onconase is now being used Phase III human clinical trials against pancreatic and liver cancer.

In general, Onconase appears to be relatively safe to use as a chemotherapeutic in humans. It does not cause any of the major toxicities associated with conventional cytotoxic drugs, such as myelosuppression, gastrointestinal toxicity, or mucositis. Approximately one third of patients treated with Onconase developed flu-like symptoms and Grade 3 arthralgia with or without peripheral edema. The most serious complication associated with administration of Onconase is decreased renal function, which was observed in Phase I dose-ranging trials. The decreased renal function was reversible upon dose reduction.

In addition to treating various types of cancers, ribonucleases may have utility in the treatment of persons infected with HIV. Noncytotoxic concentrations of Onconase have been reported to significantly inhibit HIV production in several human cell lines persistently infected with HIV.

The cytotoxicity of ribonucleases was first demonstrated in solid tumors injected with milligram quantities of bovine pancreatic ribonuclease A (RNase A; EC3.1.27.5) (Ledoux, L. Nature 176:36–37, 1955; Ledoux, L. Nature 175:258–259). Smaller doses were found to have no effect on the tumors (de Lamirande, Nature 192:52–54, 1961). A ribonuclease that is cytotoxic at low levels was discovered in bull seminal plasma (Floridi et al., Ital. Biol Sper. 43:32–36, 1967; Dostal et al.,J. Reprod. Fertil. 33:263–274, 1973). A ribonuclease with even greater cytotoxicity was isolated from frog eggs (Ardelt et al., J. Biol. Chem. 266:245–251, 1991), and this ribonuclease is the one now being tested in clinical trials under the name Onconase.

Ribonucleases catalyze the degradation of RNA. It has been demonstrated that the ribonucleolytic activity of cytotoxic ribonucleases is required for cytotoxicity (Kim et al., J. Biol. Chem. 270:10525–10530, 1995; (Ardelt et al., J. Biol. Chem. 266:245–251, 1991). Although the cytotoxicity of ribonucleases requires ribonucleolytic activity, ribonucleolytic activity alone is not sufficient to explain differential cytotoxicities observed among ribonucleases. For example, the ribonucleolytic activity of RNase A is approximately 1000-fold greater than that of Onconase, but Onconase has much greater cytotoxicity than RNase A. Thus, other properties of the enzymes must account for this difference.

Vertebrate cells contain a ribonuclease inhibitor (RI) that protects the cells from the potentially lethal effects of ribonuclease. The RI is a 50-kDa cytosolic protein that binds to ribonucleases with varying affinity. For example, RI binds to members of the bovine pancreatic ribonuclease A (RNase A) superfamily of ribonucleases with inhibition constants that span ten orders of magnitude, with $K_i$s ranging from $10^{-6}$ to $10^{-16}$M.

The cytotoxicity of a ribonuclease appears to be inversely related to the strength of the interaction between RI and the ribonuclease. For example, RNase A, which binds RI with a high affinity ($K_i=10^{-14}$M) is not cytotoxic. In contrast, Onconase binds RI with relatively low affinity ($K_i \geq 10^{-6}$M)

Some natural ribonucleases do not bind to RI. Bovine seminal ribonuclease (BS-RNase) is 80% identical in amino acid sequence to RNase A, but unlike RNase A, BS-RNase exists in a dimeric form. It has been shown that the quaternary structure of BS-RNase prevents binding by RI, thereby allowing the enzyme to retain its ribonucleolytic activity in the presence of RI (Kim et al., Biochem. J. 308:547–550, 1995; Kim et al., J. Biol. Chem. 270:10525–10530, 1995; Kim et al., J. Biol. Chem. 270:31097–31102, 1995). Onconase, a 104 amino acid residue protein that shares a high degree of homology with Rnase A, is nevertheless resistant to binding by RI. The RI-Onconase complex has a $K_d$ of $\geq 10^{-6}$M (Boix et al., J. Mol. Biol. 257:992–1007, 1996), which is at least one hundred million times less than that of the RI-RNase A complex.

Thus, the key distinction between Onconase and RNase A that accounts for the differential cytotoxicity observed in these ribonucleases is that Onconase is resistant to inhibition by RI. Normal cells produce an RI that binds ribonucleases noncovalently with a 1:1 stoichiometry and inhibits ribonucleolytic activity. The lower binding affinity of Onconase for RI prevents effective inhibition of the ribonucleolytic activity. This is the best explanation for the observed fact that Onconase is cytotoxic while ribonuclease A is not.

Recent studies in which the plasma clearance and tissue distribution of Onconase and RNase A in mice were examined showed that at three hours after the injection of Onconase or RNase A, 57of Onconase is found in the kidney, whereas only 0.9% of human pancreatic ribonuclease is found in the kidney (Sung, et al. Cancer Res. 56:4180, 1996). The decreased renal function observed in patients who receive Onconase may be a consequence of an inability to effectively clear the Onconase protein from the kidneys.

A preferred therapeutic ribonuclease would be a cytotoxic ribonuclease that can be cleared from the kidneys more readily than Onconase. A cytotoxic ribonuclease that is readily cleared from the kidneys would be less likely to cause renal toxicity. Because reduced renal function is dose-limiting for Onconase, a cytotoxic ribonuclease that does not interfere with renal function would potentially offer the advantage of greater flexibility in determining optimal dosages. A ribonuclease with lower toxicity could be administered at higher doses where indicated, e.g., for those cases in which increased dosages would afford a more effective treatment for particular types of cancers or for particular individuals.

The side effects experienced by participants in clinical trials of Onconase are symptoms that are commonly associated with immune reactions. It is reasonable to expect that a ribonuclease from a species more closely related to humans than is the leopard frog would be less likely to cause an immune reaction. Less likely still to evoke an immune response would be a human ribonuclease. The intensity of an immune reaction may also be greater when larger amounts of the immunogenic protein are administered. Therefore, a cytotoxic ribonuclease with a higher specific activity than that of Onconase may potentially be a more effective chemotherapeutic. It may be possible to achieve effective cytotoxicity with the administration of smaller amounts of protein, thereby reducing the incidence and severity of symptoms associated with an immune reaction.

New cytotoxic ribonucleases with antitumor activity are needed to enhance the spectrum of chemotherapeutics available for treatment of human cancers.

BRIEF SUMMARY OF THE INVENTION

It is an object of the present invention to provide a novel, cytotoxic, ribonuclease that has potential usefulness in the treatment of human disease.

It is an object of the present invention to provide a method for modifying the amino acid sequence of a wild-type ribonuclease to produce a novel, cytotoxic, ribonuclease.

The present invention is a ribonuclease having a modified amino acid sequence, wherein the modified ribonuclease retains its ribonucleolytic activity, and wherein the modified ribonuclease has a lower binding affinity for RI than that of the unmodified ribonuclease and retains wild-type ribonucleolytic activity.

The present invention is a method for modifying the amino acid sequence of a ribonuclease to produce a modified ribonuclease, wherein the modified ribonuclease retains its ribonucleolytic activity, and wherein the modified ribonuclease has a binding affinity for RI that is lower than that of the unmodified ribonuclease and retains wild-type ribonucleolytic activity.

The present invention is also a method for inhibiting the proliferation of cancer cells, comprising delivering to the cells an effective amount of a modified ribonuclease, wherein the modified ribonuclease has a binding affinity for RI that is lower than that of the unmodified ribonuclease and retains wild-type ribonucleolytic activity.

Other objects, advantages, and features of the present invention will become apparent after review of the specification, drawings, and claims.

DETAILED DESCRIPTION OF THE INVENTION

Figure 1:
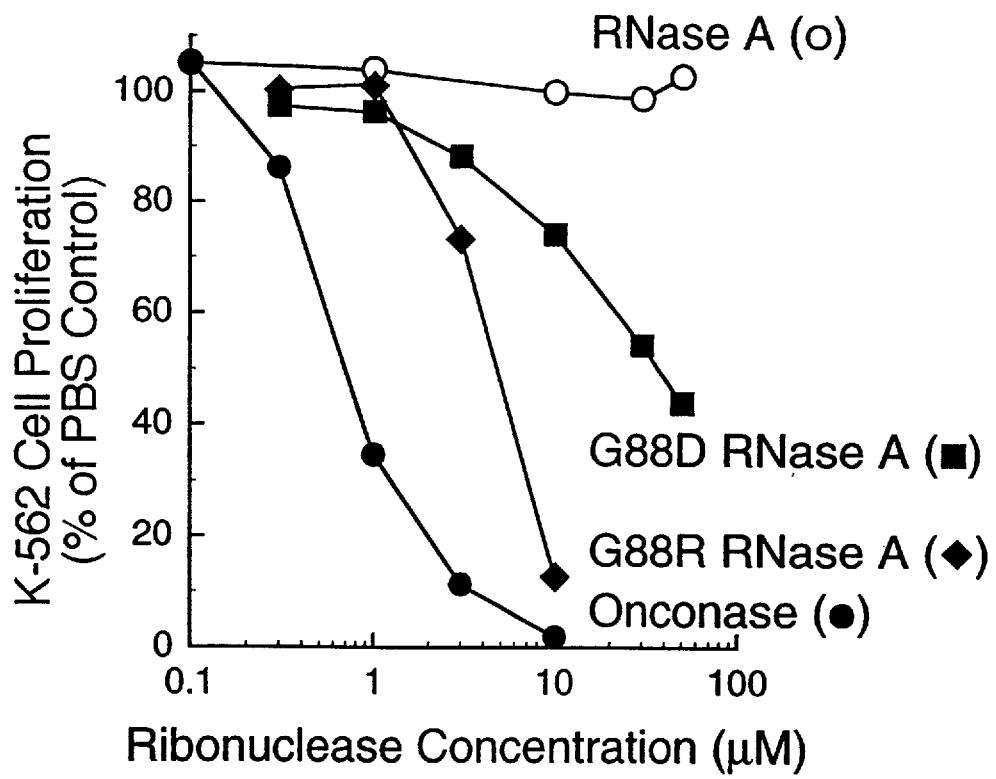
FIG. 1 shows viability of tumor cells treated with different ribonucleases.

The present invention is a modified engineered ribonuclease having an amino acid sequence that differs in at least one amino acid residue from the amino acid sequence of the corresponding wild-type ribonuclease, the wild-type ribonuclease being a member of the RNase A superfamily of ribonucleases. The modified ribonuclease retains its ribonucleolytic activity, the binding affinity of the modified ribonuclease for ribonuclease inhibitor is decreased relative to the binding affinity of unmodified ribonuclease for ribonuclease inhibitor, and the modified ribonuclease exhibits increased cytotoxic activity.

Described in the examples below are the design, production, and characterization of G88R RNase A and G88D RNase A, two modified bovine pancreatic ribonuclease A molecules that have reduced RI binding affinity, wild-type ribonucleolytic activity, and enhanced cytotoxicity. The observation and methodology of this specification may be applied to any ribonuclease of the RNase A superfamily.

Any amino acid substitution that lowers the binding affinity of the ribonuclease for RI, and which does not interfere with ribonucleolytic activity, can be used in the practice of the present invention. It has been found that one particular locus in the enzyme can be effectively altered to reduce affinity with RI. G88R RNase A has an arginine residue in place of the glycine residue at amino acid residue 88. Similarly, the glycine residue at amino acid residue 88 of G88D RNase A is replaced with an aspartate residue. The substitution of other amino acid residues at a position corresponding to amino acid residue 88 of bovine pancreatic ribonuclease A will result in altered binding affinity for RI, particularly if the amino acid residue has a charged side chain. Substitutions near this amino acid residue 88 which provide steric inhibition with binding to RI will be effective as well.

Other modifications to the amino acid sequence of bovine pancreatic ribonuclease A that occur in a loop region defined by amino acid residues 85–94 and which create such steric interference will produce modified ribonucleases having reduced binding affinity for RI, wild-type ribonucleolytic activity, and enhanced cytotoxicity. It is also anticipated that other covalently attached moieties or side chains, such as a saccharide side chain, attached to the protein in this region to provide steric inhibition will work as well.

The oligonucleotides used to obtain G88R RNase A and G88D RNase A are shown in SEQ ID NO:1 and SEQ ID NO:2, respectively. In view of the degeneracy of the genetic code, it is well known that other oligonucleotides could be used to obtain a modified ribonuclease identical to G88R RNase A or G88D RNase A. The present invention is intended to encompass a modified ribonuclease having an amino acid substitution at the amino acid residue corresponding to position 88 of bovine pancreatic Rnase A, without regard for the means by which the modified ribonuclease was obtained. It is expected that in addition to bovine pancreatic RNase A, other members of the RNase A superfamily of ribonucleases can be used in the practice of the invention. It is expected that a modification to a ribonuclease other than bovine pancreatic RNase A that occurs in a loop region corresponding to amino acid residues 85 through 94 of bovine pancreatic RNase A will produce a ribonuclease having reduced affinity for RI, wild-type ribonucleolytic activity, and increased cytotoxicity. By "a loop region corresponding to amino acid residues 85 through 94 of bovine pancreatic Rnase A" it is meant a loop having about 10–12 amino acid residues that is defined by disulfide bonds formed between two cysteine residues, wherein the loop region begins about 75–85 amino acid residues from the N-terminal end of the ribonuclease and which sequence by "best fit" amino acid sequence corresponds to residues 85 and 94 of bovine RNase A.

The Rnase A superfamily of ribonucleases constitutes a group of homologous (i.e., evolutionarily related) proteins from many mammalian, avian, reptilian, and amphibian sources. These proteins have a similar fold of their polypeptide chains, and catalyze the cleavage of RNA. A description of this superfamily can be found in Beintema et al. *Ribonucleases: Structures and Functions* 1997 pp 245–269, which is hereby incorporated by reference.

There are five exemplary human homologs of bovine pancreatic ribonuclease A that are expected to be useful in the development of cytotoxic ribonucleases for use in the treatment of human disease. Each of these five homologs has a conserved loop region analogous to the 10-amino acid residue loop region of RNase A (Table 1).

This structure showed that 24 of the 124 amino acid residues of RNase A contacted RI. Some regions of RNase A that contact RI were found to be distinct from the catalytic site.

To further define the role of the RI-ribonuclease interaction in ribonuclease cytotoxicity, site-directed mutagenesis was employed as detailed in the examples below. Briefly, ribonuclease-encoding DNA sequences were specifically altered such that expression of the sequence resulted in novel ribonucleases containing specific amino acid substitutions. Various altered sequences were developed in which a codon specifying an arginine or aspartate residue was substituted for a codon specifying one of three amino acid

TABLE 1

| Enzyme | Aligned Sequence | Seq ID No. |
|---|---|---|
| bovine pancreatic ribonuclease A | (C) R E T G S S K Y P N (C)<br>84 85 86 87 88 89 90 91 92 93 94 95 | 3 |
| human pancreatic ribonuclease | (C) R L T N G S R Y P N (C)<br>84 85 86 87 88 89 90 91 92 93 94 95 | 4 |
| human angiogenin | (C) K L H G G S P W P P (C)<br>82 83 84 85 86 87 88 89 90 91 92 93 | 5 |
| human eosinophil cationic protein | (C) D L I N P G A Q N I S N (C)<br>83 84 85 86 87 88 89 90 91 92 93 94 95 96 | 6 |
| human eosinophil derived neurotoxin | (C) N L T T P S P Q N I S N (C)<br>83 84 85 86 87 88 89 90 91 92 93 94 95 96 | 7 |
| human ribonuclease 4 | (C) R D T G S S R A P N (C)<br>81 82 83 84 85 86 87 88 89 90 91 92 | 8 |

By "enhanced cytotoxicity" it is meant that the modified ribonuclease exhibits greater cytotoxicity than the corresponding unmodified ribonuclease. In the examples below, cytotoxicity was evaluated using the human erythroleukemia cell line K-562. It is anticipated that the modified ribonuclease of the present invention is cytotoxic against other tumor cells in addition to K-562 cells.

Inhibition of cell proliferation is determined by calculating the percentage of viable K-562 cells treated with the modified or unmodified ribonuclease, where 100% viability is considered to be the number of viable cells that were treated with a solution of phosphate-buffered saline (PBS).

Preferably, the modified ribonuclease reduces cell viability by at least about 10%. More preferably, the modified ribonuclease reduces cell viability by at least about 20%. Most preferably, the modified ribonuclease reduces cell viability by about 50%, or even as much as about 75%.

The present invention is also a method for inhibiting the proliferation of tumor cells comprising providing a modified cytotoxic ribonuclease and delivering an effective amount of the ribonuclease to the tumor cells.

By "effective amount" is meant that amount of ribonuclease needed to cause a significant reduction in the proliferation of the tumor cells.

Several species of modified bovine pancreatic ribonuclease A were designed and produced using oligonucleotide-mediated site-directed mutagenesis, as described in the examples below. Each modified ribonuclease has an amino acid sequence that differs from the amino acid sequence of wild-type bovine pancreatic ribonuclease A at a single amino acid residue. It is anticipated that modified ribonucleases having multiple substitutions can also be useful in the practice of the present invention.

RI binds RNase A noncovalently with a 1:1 stoichiometry. The three-dimensional structure of the complex between RI and RNase A has been determined to a resolution of 2.5 Å (R-factor 19.4%) (Kobe et al., *Nature* 374:183–186, 1995).

residues that were found to form multiple contacts with RI residues. The introduction of an Arg or Asp residue was expected to cause both steric and electrostatic repulsion between RI and RNase A. It was hoped that this would result in a lowered binding affinity of the RNase A mutants for RI.

Materials and Methods

DNA Mutagenesis

Modification of an RNase A by site-directed mutagenesis is described in detail in U.S. Pat. No. 5,389,537, incorporated by reference herein. A cDNA that encodes RNase A was ligated to the MscI and SalI sites in the pET22B(+) expression vector (Novagen, Inc., Madison, Wis.) The plasmid, designated pBXR (delCardayré, et al. *Protein Engng* 8:261–273, 1995) directs expression of RNase A in *E. coli*. Oligonucleotide-mediated site-directed mutagenesis (Kunkel et al., 1987) of the plasmid pBXR was used to generate modified RNase A molecules having a specific amino acid substitution at a particular location. A modified RNase A having an arginine substitution at residue 88 was designated G88R RNase A, and a modified RNase having an aspartate substitution at residue 88 was designated G88D RNase A. The oligonucleotide used to obtain G88R RNase A is shown in SEQ ID NO:1, and the oligonucleotide used to obtain G88D is shown in SEQ ID NO:2. Similarly, using specially designed oligonucleotides, the aspartate residue at amino acid residue 38 was replaced with an arginine residue (D38R RNase A),and the alanine residue at amino acid residue 109 was replaced with an arginine residue (A109R RNase A).

Purification of the protein variants

The RNase A mutants were purified essentially as described previously (delCardayré, et al. *Protein Engng* 8:261–273, 1995). Onconase was purified from the eggs of the Northern leopard frog as described by Wu et al. (*J. Biol. Chem.* 268:10686–10693, 1993). Alternatively, Onconase was purified from an *E. coli* expression system essentially as described by Coix et al. (*J. Mol. Biol.* 257:992–1007).

Ribonucleolytic Activity

The ability of mutant ribonucleases to catalyze the cleavage of polymeric RNA was determined by UV spectroscopy, as described previously (delCardayré & Raines, Biochemistry, 33:6031–6037, 1994; delCardayré & Raines, J. Mol. Biol. 252:328–336, 1995).

Antitumor activity assay

The ribonuclease antitumor activity was evaluated as described previously (Kim, et al. J. Biol. Chem. 270:10525–10530, 1995). Onconase was included as a positive control and unmodified bovine pancreatic ribonuclease A was included as a negative control. The effect of various ribonucleases on the proliferation of human myeloid leukemia cell line K-562 (ATCC #CCL-243) was assessed as follows. Cells were maintained according to ATCC recommendations with the addition of antibiotics. Ribonuclease cytotoxicity toward K-562 cells was evaluated by measuring [$^3$H]-thymidine incorporation into newly synthesized DNA. Briefly, K-562 cells ($0.5 \times 10^4$ per well) were seeded into 96-well microtiterplates in 95-μl volumes. Cells were cultivated in the presence of ribonucleases for 44 h, followed by a 4 h pulse with [$^3$H]-thymidine (0.2 μCi). Cells were then harvested onto glass fiber filters using a PHD cell harvester (Cambridge Technology, Inc.; Cambridge, Mass.) and lysed by passing several ml of water through the filters. DNA and other cellular macromolecules are retained by the filter, whereas small molecules, including unincorporated label, pass through the filters. After washing extensively with water, the filters were dried with methanol and counted using a liquid scintillation counter.

The incorporation of [$^3$H]-thymidine actually measures new DNA synthesis. Reduced incorporation of [$^3$H]-thymidine reflects cytostasis, rather than cell death. By other assays, however, Onconase has been shown to cause cell death (Wu et al., J. Biol. Chem. 268:10686–10695).

Binding affinity for RI

The binding affinities of the various mutants of RNase was assessed qualitatively by a gel-based assay (Wu et al., J. Biol. Chem. 268:10686–10693) and evaluated quantitatively (Stone & Hofsteenge, Biochemistry 25:4622–4628).

Determination of thermal stability

The thermal stability of the mutant ribonucleases was evaluated to determine whether the mutants would be able to withstand exposure to relatively high temperatures (37° C.). Mutants having lowered melting temperatures may denature and lose activity. The thermal stability of each mutant ribonuclease was determined by using ultraviolet or circular dichromisim spectroscopy to evaluate $T_m$, which is the temperature at which the protein is half folded and half unfolded.

Results

Arginine substitutions for Asp 38 (D38R RNase A) and Ala 109 (A109R RNase A) were found to have little or no effect on the binding affinity of these mutants for RI. The ribonucleolytic activity of these mutants was reduced in the presence of RI. In contrast, mutant RNase A's in which an arginine or aspartate was substituted for Gly 88 (G88R RNase A and G88D RNase A, respectively) were found to have reduced binding affinity for RI, and these mutants remained catalytically active in the presence of RI (Table 2).

TABLE 2

| Ribonuclease | Ribonucleolytic | RI-Evasive | Cytotoxic |
|---|---|---|---|
| RNase A | Yes | No | No |
| D38R RNase A | Yes | No | No |
| G88R Rnase A | Yes | Yes $K_1 = 4 \times 10^{-10}$M | $IC_{50} = 5$ μM |
| G88D RNase A | Yes | Yes $K_1 = 5 \times 10^{-11}$M | $IC_{50} = 35$ μM |
| A109R Rnase A | Yes | No | No |
| ONC | Yes | Yes $K_i \geq 10^{-6}$M | $IC_{50} = 0.7$ μM |

The mutant RNase A's G88R and G88D were toxic to human myeloid leukemia cell line K-562, whereas D38R RNase A and A109R RNase A were not cytotoxic (FIG. 1). The mutant G88R RNase A was about as effective as Onconase in inhibiting cellular proliferation. G88R RNase A had an $IC_{50}$ of 5 μM, whereas Onconase had an $IC_{50}$ of 0.7 μM (Table 2). These results show that the binding affinity of a ribonuclease for RI can be modified to enhance cytotoxicity. Modified ribonucleases that retain catalytic activity in the presence of RI are effective cytotoxins.

In order to be effective in the treatment of cancer, cytotoxic ribonucleases must be stable at body temperature. Because amino acid substitutions can make proteins more sensitive to heat denaturation, the thermostability of the modified ribonucleases was evaluated. The arginine substitutions and the aspartate substitution were found to have minimal effects on the thermal stability of the enzymes (Table 3).

TABLE 3

| Ribonuclease | Thermal Stability ($T_m$; °C.) |
|---|---|
| RNase A | 64 |
| D38R RNase A | 59 |
| G88R RNase A | 60 |
| G88D RNase A | 64 |
| A109R RNase A | 64 |
| ONC | 90 |

To inhibit proliferation of tumor cells, it is expected that the modified ribonuclease of the present invention can be delivered by any standard method. Commonly employed delivery modes include intramuscular, intravenous, intraperitoneal, and direct injection into the tumor. The ribonuclease may be combined with any pharmacological carrier that does not interfere with the ribonuclease activity and which is suitable for the selected mode of delivery.

We claim:

1. An engineered ribonuclease of the RNase A superfamily having at least one amino acid substitution in a loop region functionally equivalent to amino acid residues 85–94 of bovine pancreatic RNase A, the engineered ribonuclease having reduced binding affinity for ribonuclease inhibitor, the modified ribonuclease retaining ribonucleolytic activity.

2. The ribonuclease of claim 1, wherein the modified ribonuclease is derived from bovine pancreatic ribonuclease A.

3. The ribonuclease of claim 2, wherein the glycine residue at amino acid position 88 of bovine pancreatic ribonuclease A is substituted for a positively charged amino acid residue.

4. The ribonuclease of claim 3, wherein the positively charged amino acid residue is arginine.

5. The ribonuclease of claim 2, wherein the glycine residue at amino acid position 88 of bovine pancreatic ribonuclease A is substituted for a negatively charged amino acid residue.

6. The ribonuclease of claim 5, wherein the negatively charged amino acid residue is aspartate.

7. A modified ribonuclease A of the RNase A superfamily, the modified ribonuclease A engineered by human modification thereof, the modified ribonuclease A having an alteration to its structure as compared to a corresponding wild-type ribonuclease A, the alteration being (1) in the region corresponding to amino acid residues 85–94 of bovine pancreatic RNase A, and (ii) the modification providing steric or electrostatic hindrance to binding by ribonuclease inhibitor.

8. A method for inhibiting the proliferation of tumor cells, comprising providing a modified ribonuclease of claim 7 and delivering an effective amount of the modified ribonuclease to the tumor cells.

9. A method for creating novel engineered ribonuclease A molecules having cytotoxic properties comprising the steps of creating an altered gene encoding a ribonuclease A, the gene having an alteration in the coding region corresponding to amino acids 85 to 94 of bovine pancreatic ribonuclease A, expressing the altered gene in a suitable host cell, and testing the affinity of the expressed ribonuclease A for ribonuclease inhibitor.

* * * * *

SEQUENCE LISTING ( 1 ) GENERAL INFORMATION:

( i i i ) NUMBER OF SEQUENCES: 8

( 2 ) INFORMATION FOR SEQ ID NO:1:

( i ) SEQUENCE CHARACTERISTICS:
    ( A ) LENGTH: 20 base pairs
    ( B ) TYPE: nucleic acid
    ( C ) STRANDEDNESS: single
    ( D ) TOPOLOGY: linear ( i i ) MOLECULE TYPE: DNA (genomic)

( x i ) SEQUENCE DESCRIPTION: SEQ ID NO:1:

TTGGAGCTAC GCGTCTCACG    20

( 2 ) INFORMATION FOR SEQ ID NO:2:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:2:

CTTGGAAGAG TCGGTCTC    18

( 2 ) INFORMATION FOR SEQ ID NO:3:

( i ) SEQUENCE CHARACTERISTICS:
        ( A ) LENGTH: 12 amino acids
        ( B ) TYPE: amino acid
        ( C ) STRANDEDNESS:
        ( D ) TOPOLOGY: linear ( i i ) MOLECULE TYPE: peptide ( x i ) SEQUENCE DESCRIPTION: SEQ ID NO:3:

Cys Arg Glu Thr Gly Ser Ser Lys Tyr Pro Asn Cys
1                5                      10

( 2 ) INFORMATION FOR SEQ ID NO:4:

( i ) SEQUENCE CHARACTERISTICS:
        ( A ) LENGTH: 12 amino acids
        ( B ) TYPE: amino acid
        ( C ) STRANDEDNESS:
        ( D ) TOPOLOGY: linear ( i i ) MOLECULE TYPE: peptide ( x i ) SEQUENCE DESCRIPTION: SEQ ID NO:4:

Cys Arg Leu Thr Asn Gly Ser Arg Tyr Pro Asn Cys
1                5                      10

( 2 ) INFORMATION FOR SEQ ID NO:5:

( i ) SEQUENCE CHARACTERISTICS:
        ( A ) LENGTH: 12 amino acids
        ( B ) TYPE: amino acid
        ( C ) STRANDEDNESS:
        ( D ) TOPOLOGY: linear ( i i ) MOLECULE TYPE: peptide ( x i ) SEQUENCE DESCRIPTION: SEQ ID NO:5:

Cys Lys Leu His Gly Gly Ser Pro Trp Pro Pro Cys
1                5                      10

( 2 ) INFORMATION FOR SEQ ID NO:6:

( i ) SEQUENCE CHARACTERISTICS:

-continued

```
         ( A ) LENGTH: 14 amino acids
         ( B ) TYPE: amino acid
         ( C ) STRANDEDNESS:
         ( D ) TOPOLOGY: linear ( i i ) MOLECULE TYPE: peptide ( x i ) SEQUENCE DESCRIPTION: SEQ ID NO:6:

Cys  Asp  Leu  Ile  Asn  Pro  Gly  Ala  Gln  Asn  Ile  Ser  Asn  Cys
    1                   5                        10

( 2 ) INFORMATION FOR SEQ ID NO:7:

( i ) SEQUENCE CHARACTERISTICS:
         ( A ) LENGTH: 14 amino acids
         ( B ) TYPE: amino acid
         ( C ) STRANDEDNESS:
         ( D ) TOPOLOGY: linear ( i i ) MOLECULE TYPE: peptide ( x i ) SEQUENCE DESCRIPTION: SEQ ID NO:7:

Cys  Asn  Leu  Thr  Thr  Pro  Ser  Pro  Gln  Asn  Ile  Ser  Asn  Cys
    1                   5                        10

( 2 ) INFORMATION FOR SEQ ID NO:8:

( i ) SEQUENCE CHARACTERISTICS:
         ( A ) LENGTH: 12 amino acids
         ( B ) TYPE: amino acid
         ( C ) STRANDEDNESS:
         ( D ) TOPOLOGY: linear ( i i ) MOLECULE TYPE: peptide ( x i ) SEQUENCE DESCRIPTION: SEQ ID NO:8:

Cys  Arg  Asp  Thr  Gly  Ser  Ser  Arg  Ala  Pro  Asn  Cys
    1                   5                        10
```